United States Patent
Toker et al.

(10) Patent No.: US 7,253,891 B2
(45) Date of Patent: Aug. 7, 2007

(54) METHOD AND APPARATUS FOR SIMULTANEOUS 2-D AND TOPOGRAPHICAL INSPECTION

(75) Inventors: Gregory Toker, Jerusalem (IL); Andrei Brunfeld, Cupertino, CA (US); Ilia Lutsker, Kfar Saba (IL)

(73) Assignee: Orbotech Ltd., Yavne (IL)

( * ) Notice: Subject to any disclaimer, the term of this patent is extended or adjusted under 35 U.S.C. 154(b) by 307 days.

(21) Appl. No.: 10/753,391

(22) Filed: Jan. 9, 2004

(65) Prior Publication Data

US 2004/0156043 A1   Aug. 12, 2004

Related U.S. Application Data

(60) Provisional application No. 60/438,783, filed on Jan. 9, 2003.

(51) Int. Cl.
*G01B 11/24* (2006.01)
*G01N 21/88* (2006.01)

(52) U.S. Cl. .................. 356/237.2; 356/606; 356/602; 250/216; 250/548

(58) Field of Classification Search .. 356/237.1–237.6, 356/614, 625, 628, 635; 250/216, 208.1, 250/559.4, 559.45, 559.21; 382/114, 145, 382/1, 8
See application file for complete search history.

(56) References Cited

U.S. PATENT DOCUMENTS

| | | | |
|---|---|---|---|
| 4,741,621 A * | 5/1988 | Taft et al. .................... 356/606 |
| 4,845,373 A * | 7/1989 | Jamieson et al. ........... 250/548 |
| 5,058,178 A * | 10/1991 | Ray ............................. 382/150 |
| 5,127,061 A * | 6/1992 | Amir et al. .................. 382/154 |
| 5,166,985 A * | 11/1992 | Takagi et al. ................ 382/150 |
| 5,189,481 A * | 2/1993 | Jann et al. ..................... 356/73 |
| 5,293,324 A * | 3/1994 | Tokura ......................... 382/141 |
| 5,638,175 A | 6/1997 | Brunfeld et al. |
| 5,761,337 A * | 6/1998 | Nishimura et al. ......... 382/150 |
| 5,774,572 A * | 6/1998 | Caspi .......................... 382/141 |
| 5,798,829 A | 8/1998 | Vaez-Iravani |
| 6,437,312 B1 * | 8/2002 | Adler et al. ................. 250/216 |
| 6,496,254 B2 | 12/2002 | Bostrom et al. |
| 6,521,866 B1 * | 2/2003 | Arai et al. .............. 219/121.73 |
| 6,552,783 B1 | 4/2003 | Schmidt et al. |
| 6,587,600 B1 * | 7/2003 | Shipley ....................... 382/284 |
| 6,621,581 B1 * | 9/2003 | Hunt et al. .................. 356/601 |
| 6,654,115 B2 * | 11/2003 | Zemer et al. ............. 356/237.5 |
| 6,806,971 B2 * | 10/2004 | Finarov ....................... 356/636 |
| 6,954,274 B2 * | 10/2005 | Sasaki et al. ................ 356/606 |
| 7,078,650 B2 * | 7/2006 | Gross et al. ........... 219/121.71 |
| 2001/0012107 A1 | 8/2001 | Toh |
| 2003/0006364 A1 | 1/2003 | Katzir et al. |

FOREIGN PATENT DOCUMENTS

WO        WO 01/50760        7/2001

* cited by examiner

*Primary Examiner*—Sang H. Nguyen
(74) *Attorney, Agent, or Firm*—Sughrue Mion, PLLC (57) ABSTRACT

Apparatus for sensing information regarding a surface including a first plurality of optical elements arranged to acquire two dimensional information about a surface, a second plurality of optical elements arranged to acquire topographical information about the surface, wherein the first plurality and the second plurality of optical elements are arranged to simultaneously provide the two dimensional information and the topographical information to at least partially non-overlapping portions of a single sensor array.

29 Claims, 8 Drawing Sheets

CROSS-SCAN DIRECTION

FIG. 6A

CROSS-SCAN DIRECTION

FIG. 6B

SCAN DIRECTION

METHOD AND APPARATUS FOR SIMULTANEOUS 2-D AND TOPOGRAPHICAL INSPECTION

This application claims the benefit of U.S. Provisional Patent Application No. 60/438,783, filed Jan. 9, 2003, the disclosure of which is incorporated by reference in its entirety.

FIELD OF THE INVENTION

The present invention generally relates to systems and methods employed in the simultaneous sensing of different characteristics of a surface of an object, and more particularly to simultaneously sensing two dimensional and topographical information about the surface, useful for inspecting the surface for defects.

BACKGROUND OF THE INVENTION

It is well know to employ automated optical inspect systems to inspect electrical circuits such as printed circuit boards (PCB) for defects at various stages of fabrication. An important stage in fabricating electrical circuits is the deposition of solder paste onto a PCB, prior to mounting of electronic devices such as microchips and other semiconductor devices. In fact, a substantial percentage of defects in electronic devices can be attributed to defects associated with problems related to the deposition of solder paste. Early identification of these problems can result in a considerable cost savings to a manufacturer of electronic devices.

Various factors are commonly recognized as determining the quality of solder paste deposits, including: position accuracy of each solder paste deposit over a solder pad; average thickness of a solder paste deposit; and differences in the volume of each solder paste deposit.

Consequently, an effective system for automatically optically inspecting solder paste deposits should to be able to precisely determine both 2 dimensional as well as topographical information (height information for various locations) relating to the surface of a printed circuit board onto which solder paste has been deposited. This information needs to be sensed and processed at a high speed in order to avoid forming a bottle neck during the assembly of electronic components onto an assembled electronic circuit device.

SUMMARY OF INVENTION

In accordance with a broad aspect of an embodiment of the invention, a system simultaneously senses different types of information about a surface using a single sensor array.

The present invention seeks to provide an improved system for simultaneously acquiring two dimensional and topographical information about a surface, particular useful for inspecting solder paste deposits for defects.

The present invention seeks to provide apparatus arranged to simultaneously sense two dimensional and topographical information about a surface at non-overlapping locations, which is imaged onto a single sensor array.

The present invention further seeks to provide apparatus for simultaneously sensing two dimensional information and topographical information about a surface, the topographical information being sensed using illumination provided from a direction generally perpendicular to the surface.

The present invention further seeks to provide apparatus arranged to illuminate a surface at a first location with illumination suitable for sensing two dimensional information about the surface, and to illuminate the surface at a second location with illumination suitable for sensing topographical information. Illumination for sensing two dimensional information comprises concentrated illumination provided at a multiplicity of angles. Illumination for sensing topographical information is provided along a direction generally perpendicular to the surface.

The present invention further seeks to provide apparatus arranged to illuminate a surface with coherent light operative to generate an extended source from a coherent light source, and then concentrate light from the extended source onto the surface.

The present invention further seeks to provide apparatus for sensing information about a surface, the surface being illuminated by light emitted from a laser which has been angularly expanded and subsequently focused onto the surface. The expansion and subsequent focusing reduces coherence of the laser illumination. The surface is imaged by a scanning sensor array having a multiplicity of pixels, such that each location on the surface is sequentially imaged by at least two pixels. Sensed values from at least two pixels are combined, thereby increasing uniformity.

There is thus provided in accordance with an embodiment of the invention apparatus for sensing information regarding a surface, including a first plurality of optical elements arranged to acquire two dimensional information about a surface a second plurality of optical elements arranged to acquire topographical information about the surface; the first plurality and the second plurality of optical elements being arranged to simultaneously provide the two dimensional information and the topographical information to at least partially non-overlapping portions of a single sensor array.

Various sub-embodiments include one or more of the following:

The first plurality of optical elements is arranged to acquire the two dimensional information from a first portion of the surface while the second plurality of optical elements acquires the topographical information from a second portion of the surface.

The first portion of the surface and the second portion of the surface are at least partially non-overlapping.

The first portion of the surface comprises a first elongated region of the surface, and the second portion of the surface comprises a second elongated region of the surface.

A displacer is operative to provide mutual displacement between the surface and the first plurality of optical elements during acquisition of the two dimensional information.

A first portion of the surface whereat two-dimensional information is acquired comprises a first elongated region of the surface, and a second portion of the surface whereat topographical information is acquired comprises a second elongated region of the surface at least partially non-overlapping with the first elongated region.

The displacer is further operative to provide mutual displacement between the surface and the second plurality of optical elements during acquisition of the topographical information.

The first plurality of optical elements comprises an imaging lens shared with the second plurality of optical elements. The imaging lens is arranged to receive acquired two dimensional information and acquired topographical information.

The imaging lens is operative to generate an image of a first portion of the surface on the sensor for acquiring two dimensional information corresponding to the first portion, and to generate an image of a line of illumination at a second portion of the surface for acquiring a topographical information corresponding to the second portion.

A first plurality of illumination optical elements is arranged to illuminate the first portion of the surface with illumination suitable for acquiring two dimensional information about the surface, and a second plurality of illumination optical elements is arranged to illuminate the second portion of the surface with illumination suitable for acquiring topographical information about the surface.

The first plurality of illumination optical elements includes at least one light emitter arranged to provide illumination at least some illumination from within a first range of converging angles relative to a first axis, and additional illumination from within a second range of converging angles relative to the first axis.

The at least one light emitter includes a plurality of laser diodes.

The illumination optical elements include a diffuser diffusing light from the at least one light emitter along a second axis generally perpendicular to the first axis.

The diffuser includes a lenticular array.

The second plurality of illumination optical elements includes at least one light emitter arranged to illuminate a linear region on the surface from a direction generally perpendicular to the surface.

The at least one light emitter includes at least one laser emitter emitting structured light.

The first plurality of optical elements is arranged to view a first portion of the surface from a direction generally perpendicular to the surface.

The second plurality of optical elements is arranged view a second portion of the surface from a direction angled with respect to the surface.

The second plurality of optical elements is arranged view a second portion of the surface from a direction angled with respect to the surface.

The first portion is illuminated by illumination provided at a plurality of angles relative to the surface.

The second portion is illuminated by illumination that is provided from a direction generally perpendicular to the surface.

An optical path distance between the first portion and the single sensor array is equal to an optical path distance between the second portion and the single sensor array.

There is thus provided in accordance with another embodiment of the invention apparatus for sensing information regarding a surface, including a first plurality of optical elements arranged to acquire two dimensional information about a surface, and a second plurality of optical elements arranged to acquire topographical information about the surface during acquisition of the two dimensional information, the second plurality of optical elements including an illuminator illuminating a first portion of the surface from a direction being generally perpendicular to the surface.

Various sub-embodiments include one or more of the following:

The first plurality of optical elements are arranged to acquire the two dimensional information from a direction being generally perpendicular to the surface.

The second plurality of optical elements are arranged to acquire the topographical information from a direction being generally non-perpendicular to the surface.

The second plurality of optical elements are arranged to acquire the topographical information from a direction being generally non-perpendicular to the surface.

The first plurality of optical elements and the beam combiner define a first optical path for viewing a first portion of the surface from a direction generally perpendicular thereto, and the second plurality of optical elements and the beam combiner define a second optical path for viewing a second portion of the surface from a generally non-perpendicular angle.

The least one sensor senses information about the surface, and a displacer is operative to displace the surface and the sensor relative to each other while the sensor is sensing the information.

The first portion and the second portion of the surface are generally non overlapping.

The at least one sensor comprises a single sensor array operative to sense two-dimensional information corresponding to the first portion at a first location in the sensor array and to sense topographical information corresponding to the second portion at a second location in the sensor array. The first location is generally non-overlapping with the second location.

There is thus provided in accordance with another embodiment of the present invention apparatus for illuminating a surface for simultaneously sensing two dimensional and topographical information regarding the surface, the apparatus including a first source of illumination illuminating a first portion of a surface with first illumination suitable for sensing two-dimensional information about the surface, the first portion being elongated along a first axis, the first illumination impinging upon the surface from within at least two different ranges of angles relative to a second axis that intersects the first axis; and a second source of illumination illuminating a second portion of the surface with second illumination suitable for sensing topographical information about the surface, the second portion being elongated along the first axis, the second illumination impinging on the surface from a direction perpendicular to the surface relative to the second axis.

Various sub-embodiments include one or more of the following:

The first portion and the second portion are non-overlapping.

A width dimension of the first portion along the second axis is wider than a width dimension of the second portion along the second axis.

A first range of angles within the at least two different ranges of angles is non overlapping with a second range of angles within the at least two different ranges of angles.

There is thus provided in accordance with another embodiment of the present invention apparatus for illuminating a surface with coherent light, including: an emitter emitting coherent light; a collimating lens collimating light emitted by the emitter; a first diffuser receiving the collimated light and spreading the collimated light at each of a multiplicity of locations along a first axis; and a cylindrical lens receiving light from the diffuser and concentrating the light onto a surface.

There is thus provided in accordance with another embodiment of the present invention apparatus for sensing information about a surface, including at least one lamp emitting coherent light; a diffuser arranged to receive the coherent light and output light appearing as emitted from a multiplicity of locations on the diffuser, light at each location being output in a plurality of directions; a lens arranged to receive light from the diffuser and to concentrate the light onto a surface; and a sensor array including a multiplicity of sensor elements, the array being arranged such that a location on the surface is sequentially sensed by at least two sensor elements.

Various sub-embodiments of the invention include one or more of the following:

The lamp includes a laser.

The laser comprises diode laser.

The diffuser comprises a lenticular array diffusing the coherent light along a first axis, but not along a second axis orthogonal to the first axis.

The lens comprises a cylindrical lens focusing light from the diffuser along the first axis.

The cylindrical lens comprises a fresnel lens.

The sensor array comprises a CMOS sensor array.

The CMOS sensor array comprises a sensor array configured to operate in a memory integration mode of operation.

BRIEF DESCRIPTION OF DRAWINGS

The present invention will be understood and appreciated more fully from the following detailed description, taken in conjunction with the drawings in which.

DETAILED DESCRIPTION

Figure 1A:
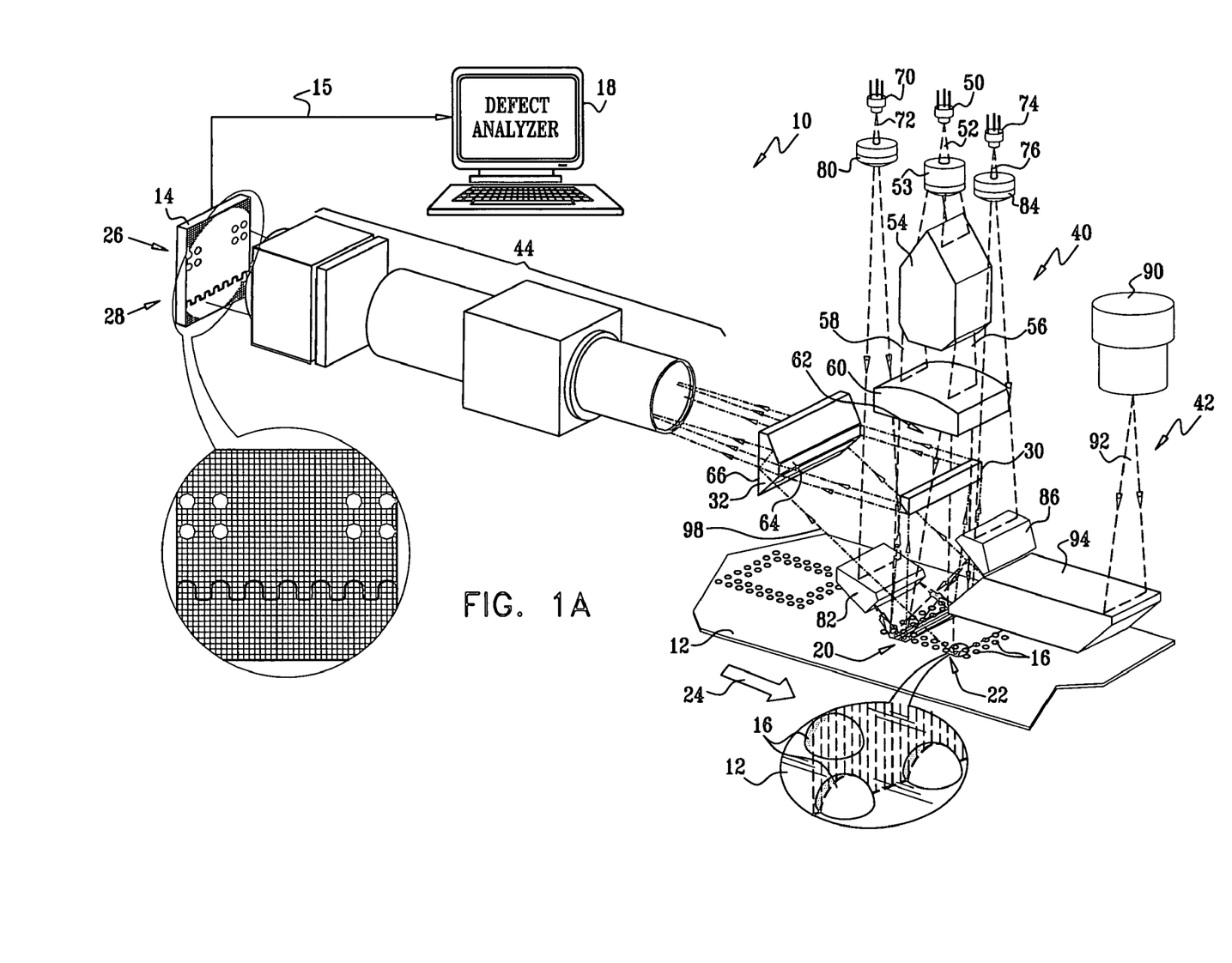
FIG. 1A is a simplified pictorial illustration of a system for sensing 2-D and topographical information of a surface in accordance with an embodiment of the invention.
Figure 1B:
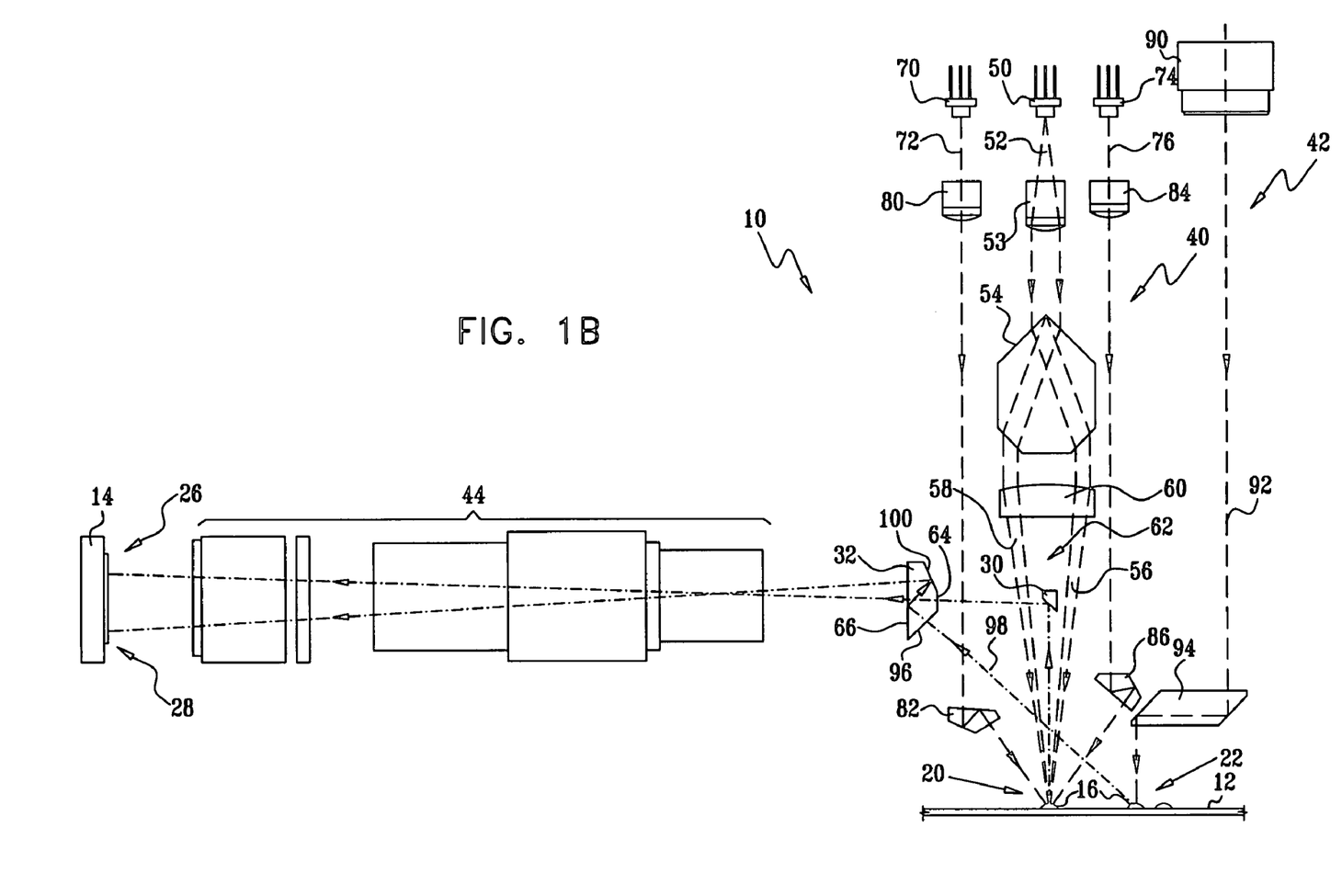
FIG. 1B is a simplified side view illustration and ray trace of the system of FIG. 1A.

Reference is made to FIG. 1A, which is a simplified pictorial illustration of a system 10 for sensing multiple characteristics of a surface 12 in accordance with an embodiment of the invention, and to FIG. 1B, which is a simplified side view illustration and ray trace of the system of FIG. 1A. System 10 is operative to sense 2-D and topographical characteristics of surface 12 and generally includes a first plurality of optical elements arranged to acquire two dimensional (2-D) information about a surface and a second plurality of optical elements arranged to acquire topographical information about the surface. The first plurality and the second plurality of optical elements are arranged to simultaneously provide the two dimensional information and the topographical information to a single sensor array 14 which senses the input information and outputs an electronic file 15 including a 2-D and topographical record of surface 12. The computer file 15 is received by a defect analyzer 18 operative to analyze the file to locate defects on surface 12.

In FIG. 1A, it is seen that some of the optical elements are used exclusively in the sensing of 2-D characteristics, some of the optical elements are used exclusively in the sensing of topographical characteristics, and some of the optical elements are used both in the sensing of 2-D and topographical characteristics. This arrangement, however, is given by way of example and other suitable combinations of optical elements may be employed. For example, the optical elements may be arranged such that optical elements are dedicated to the sensing of either 2-D or topographical information, or such that all optical elements in the system are employed in sensing both 2-D and topographical information.

In accordance with an embodiment of the invention, system 10 is employed in the inspection of solder past deposits 16 on in-fabrication electrical circuits, such as printed circuit boards. Solder paste is deposited, for example, prior to the assembly of electronic components such as integrated circuits onto the printed circuit board. The outputs of sensor array 14, for example electronic files 15, typically are provided to a defect detection computer 18 operative to analyze the outputs and indicate defects in the solder paste deposits. In an application for the inspection of solder past deposits, defects may include, for example and without limitation, improperly located solder paste deposits, solder paste deposits having an improper height dimension and solder paste deposits having an insufficient volume of solder paste.

As seen in FIG. 1A, system 10 simultaneously acquires at sensor 14 both a 2-D image of a first portion 20 of surface 12 as well as separate topographical information, for example a height profile, of a second portion 22 of surface 12. In accordance with an embodiment of the invention, a displacer (not shown) is provided to mutually displace surface 12 and system 10 relative to each other, for example as indicated by arrow 24, during acquisition of 2-D and/or topographical information regarding surface 12. It is thus appreciated that although respective first portion 20 and second portion 22 cover only a part of surface 12, by displacing system 10 and surface 12 relative to each other, 2-D and topographical information may be acquired for an entire surface. The information may be acquired in a single swath or in multiple swaths, for example in a serpentine pattern.

It is a feature of an embodiment of the present invention that both 2-D information and topographical information are sensed using the single sensor array 14. The 2-D information is sensed at one or more rows of pixels at a first location 26 on sensor array 14, using for example either single row or multiple rows of the sensor. The topographical information is sensed using several rows of pixels at a second location 28 on sensor array 14 by way of triangulation. Each row of pixels at location 28 indicates a surface height at given lateral position.

As seen in FIG. 1A, the first portion 20, defining a first elongated region on surface 12, and the second portion 22, defining a second elongated region on surface 12, are mutually set apart from each other on surface 12 and are at least partially non-overlapping. Likewise, second location 28 is set apart from the first location 26 on sensor array 14, and the two locations 26 and 28 on sensor array 14 are at least partially non-overlapping. Sensor array suitably is a high-speed CMOS type sensor, for example a model MV10_or model MV40 CMOS photosensor array available from the imaging division of Micron Technologies, Inc. of Id., USA. In an embodiment of the invention, information is read from selected pixels in the CMOS sensor. Thus, in accordance with system design, the use of all of the pixels in sensor array may not be required. Only those pixels required to sense 2-D and topographical information are actually read thereby speeding up information sensing.

In accordance with an embodiment of the invention, sensor array 14 senses 2-D information operated a memory integration mode of operation. In a memory integration mode of operation, multiple partially overlapping images are sequentially acquired and digitized during scanning. The digital images are sequentially added to memory, and digital pixel values from corresponding locations in partially overlapping images are added together to generate a composite image. A CMOS sensor operating in a memory integration mode of operation is described in greater detail copending U.S. patent application Ser. No. 10/176,003, filed Jun. 21, 2002 and entitled "Optical Sensor Array for Scanning Systems", the disclosure of which is incorporated herein in its entirety. Other suitable forms of sensing 2-D information, as know in the art, may be employed.

Topographical information is acquired using triangulation techniques, preferably employing illumination provided along an axis generally normal to surface 12.

By separating the respective portions 20 and 22 on surface 12 whereat 2-D information and topographical information are sensed, illumination for sensing 2-D and topographical information may be optimized at each portion. By employing a single sensor array 14 to sense both 2-D and topographical information regarding surface 12, in combination with appropriately corrected and aligned optics, the 2-D information and the topographic information are kept in highly precise alignment, thereby enabling a highly accurate correlation between the 2-D and topographical information. Moreover, the use of a single sensor to simultaneously sense 2-D and topographical information results in a reduced cost compared to other systems acquiring both 2-D and topographical information.

In accordance with an embodiment of the invention, two information channels, one for 2-D information and one for topographical information, are thus "multiplexed" onto the same sensor array. In the embodiment seen in FIGS. 1A and 1B, the multiplexing is achieved by spatially separating the respective 2-D and topographic channels. As seen in FIGS. 1A and 1B, illumination is provided along separate light pathways 40 and 42 to illuminate spatially separated portions 20 and 22 of surface 12. A mirror 30 and a beam combining prism 32 simultaneously deliver 2-D and topographical information from portions 20 and 22 respectively, to imaging lenses 44 and finally to sensor array 14. It is noted that in accordance with an embodiment of the invention, despite the spatial separation between portion 20, whereat 2-D information is sensed, and portion 22, whereat 2-D information is sensed, the optical path between portion 20 and sensor array 14 is equal in length to the optical path between portion 22 and sensor array 14.

Optionally, as will be further described hereinbelow, separation of the respective 2-D and topographic information channels may be done using various alternative methodologies, including without limitation, by illumination at different wavelengths, by way of polarization or by means of time-multiplexing.

In accordance with an embodiment of the invention, surface 12 is generally disposed horizontally, as is imaging lens 44. Two elongated portions of surface 12, one for 2-D imaging, designated 20, and one for height profiling by triangulation, designated 22, are illuminated.

As seen in FIGS. 1A and 1B, illumination provided along light pathway 40 illuminates portion 20 in a manner particularly suitable for sensing 2-D information. Light pathway 40 includes at least one high brightness lamp 50, suitably one or more diodes or laser diodes, outputting a beam 52. Beam 52 passes through a collimating lens 53, operative to collimate beam 52, and impinges on the vertex of a rhombus prism 54. Beam 52 is divided into two spatially separated lobes 56 and 58. Each of lobes 56 and 58 pass through a cylindrical lens 60 which directs lobes 56 and 58 to each converge at surface 12 at an angle thereby defining a wedge shaped gap 62 between the lobes.

Additional illumination is provided along light pathway 40 by at least one first outboard lamp 70 providing at least one first outboard beam 72, and at least one second outboard lamp 74 providing at least one second outboard beam 76. Lamps 70 and 74 suitably are high brightness lamps, suitably diodes or laser diodes. Beam 72 passes through one or more lenses, schematically depicted as lens 80, and a beam directing prism 82 to illuminate portion 20 from a range of angles outboard of lobe 58. Beam 76 likewise passes through one or more lenses, schematically depicted as lens 84, and a beam directing prism 86 to illuminate portion 20 from a range of angles outboard of lobe 56.

It is thus noted from FIGS. 1A and 1B that portion 20 is illuminated with illumination provided from within a first range of angles relative to an axis perpendicular to surface 12, and with additional illumination from within a second range of angles being more obtuse than the first range of angles. Preferably, the angular arrangement is generally symmetrical about the vertical axis.

As seen in FIGS. 1A and 1B, mirror 30 is disposed in gap 62 between lobes 56 and 58 to view portion 20 as illuminated by lobes 56 and 58, and by beams 72 and 76. Mirror 30 may include any suitable reflective surface, for example silvered glass or the silvered or non-silvered face of a suitably angled prism. Light from portion 20 is received by mirror 30 and passed through beam combining prism 32 at a location defined by a front surface 64 and a back surface 66, which are generally plane parallel to each other. Imaging lenses 44 thus view portion 20 and forms an image thereof on sensor array 14 at location 26.

In accordance with an embodiment of the invention, portion 22 is illuminated along light pathway 42. At portion 22 a thin elongated beam of illumination is provided along an axis generally perpendicular to surface 12. Light pathway 42 includes at least one high brightness lamp 90, suitably one or more diodes or laser diodes, outputting a structured light beam 92 having a generally uniform intensity along its entire length. Beam 92 passes through a periscope 94, operative to translate beam 92 to illuminate the appropriate portion of surface 12 along an axis generally perpendicular to surface 12. Suitable illuminators include Laseris™ structured light generators available from StockerYale, Inc.

As seen particularly in FIG. 1B, an input facet 96 of beam combining prism 32 is angled to receive an angled light input 98 received from portion 22 when illuminated by beam 92. The angled light input 98 is reflected inside beam combining prism 32 by back surface 66 by total internal reflection and by a top surface 100 to be subsequently passed through back surface 66 to impinge on imaging lenses 44. Lenses 44 thus additionally view portion 22 and at location 28 on sensor array 14 form an image of beam 92 on surface 12.

In accordance with an embodiment of the invention, back surface 66 initially reflects angled light input 98 by total internal reflection. However, the angle of top surface 100 is insufficient for total internal reflection. Consequently, a silver or other suitable reflective coating is applied to top surface 100. Upon reflection by top surface 100, light input is passed through back surface 66.

In accordance with an embodiment of the invention, the beam combining prism 32 and the relative positions of the optical components in system 10 are configured and engineered to provide an optical path between sensor and portions 20 and 22 such that both the 2-D image of portion 20 and a topographical height profile of portion 22 are simultaneously in focus at locations 26 and 28 on sensor array 14.

Figure 2A:
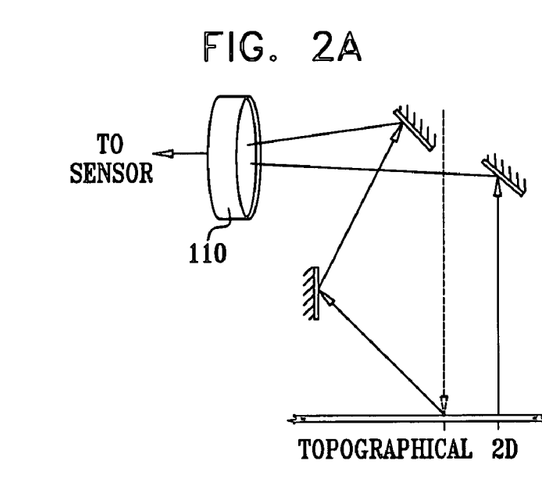
FIGS. 2A-2D are side view illustrations of a simplified architecture of a device for simultaneously sensing 2-D and topographical information of a surface at set-apart locations.
Figure 2B:
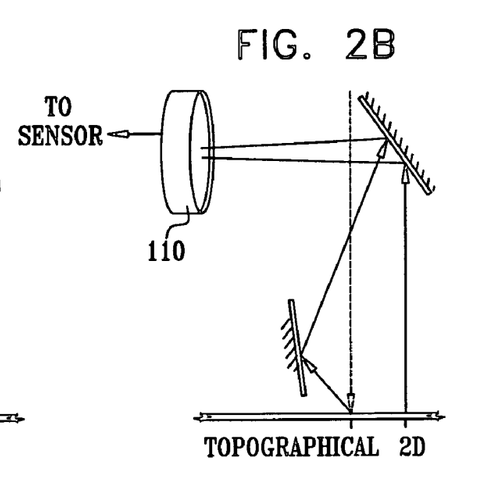
Figure 2C:
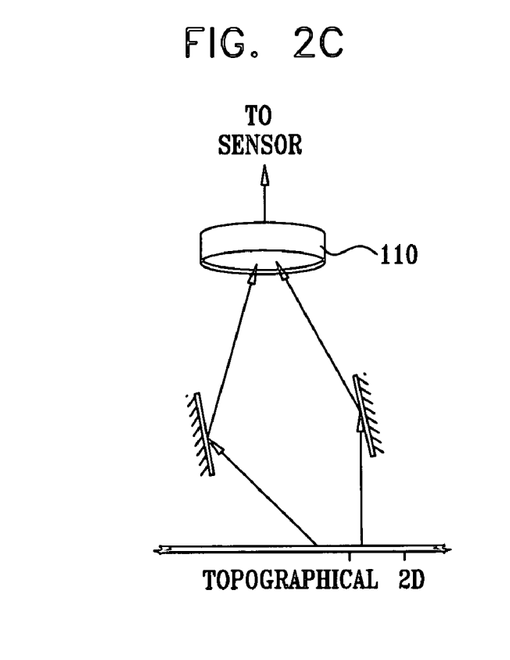
Figure 2D:
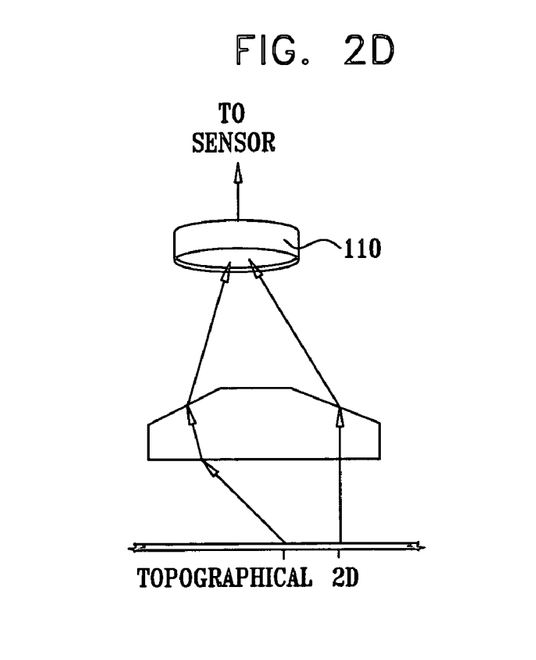

Reference is now made to FIGS. 2A-2D which are side view illustrations of a simplified architecture of devices for simultaneously sensing 2-D and topographical information of a surface at set-apart locations. These architectures constitute alternative configurations of devices operative to acquire multiplexed information, for example a 2-D information and topographical information, from spatially separated portions of a surface. FIGS. 2A-2D show only simultaneous sensing of multiplexed information. An illumination device associated therewith is not shown. In each of the devices seen in FIGS. 2A-2C, mirrors are provided to reflect sensed information in each of the respective 2-D and topographical sensing channels. In FIG. 2D, a prism is provided to direct sensed information in each of the respective 2D and topographical sensing channels. The sensed information is directed to the same lens 110 which passes the sensed information to the same sensor located in an image plane.

Figure 3:
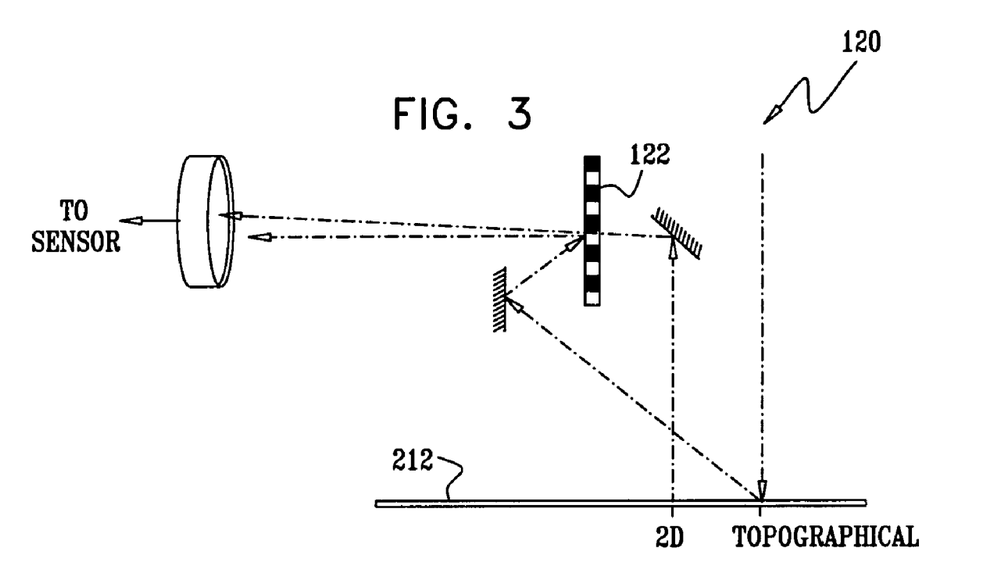
FIG. 3 is a side view illustration of a simplified architecture of another device for simultaneously sensing 2-D and topographical information of a surface at set-apart locations.

Reference is now made to FIG. 3 which is a side view illustration of a simplified architecture of another device 120 for simultaneously sensing 2-D and topographical information of a surface at set-apart locations. In FIG. 3, only the principal rays are shown, and the source of illumination is shown only for the channel in which topographical information is sensed.

Information from the respective 2-D and topographical information channels is combined using a suitable beam combiner 122 such as a partially reflective mirror, grating, dichroic filter, or fully reflecting mirror having an aperture enabling sensed 2-D information to pass through the beam combiner.

In accordance with an embodiment of the invention, beam combiner is a dichroic filter. Separation of the respective 2-D and topographical channels is accomplished using light of different wavelengths. In this manner, it is appreciated that the respective portions of surface 212 whereat 2-D and topographical information is sensed may be spatially separated as seen in FIG. 3, however when chromatically separated, spatial separation is less crucial and simultaneous sensing of 2-D and topographical information may be accomplished without spatial separation.

Figure 4:
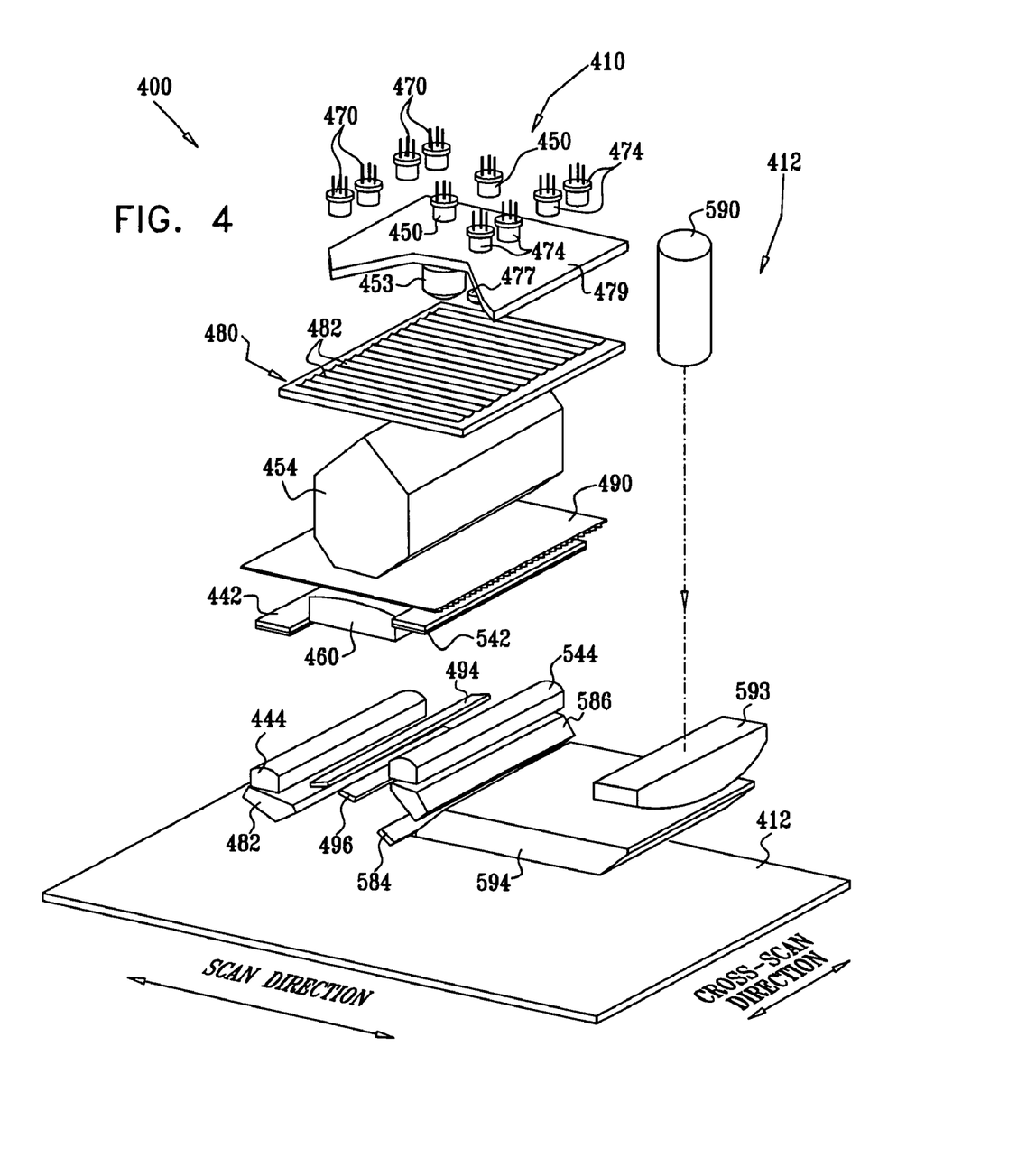
FIG. 4 is a simplified pictorial illustration of an illumination system usable in the system of FIG. 1A.
Figure 5A:
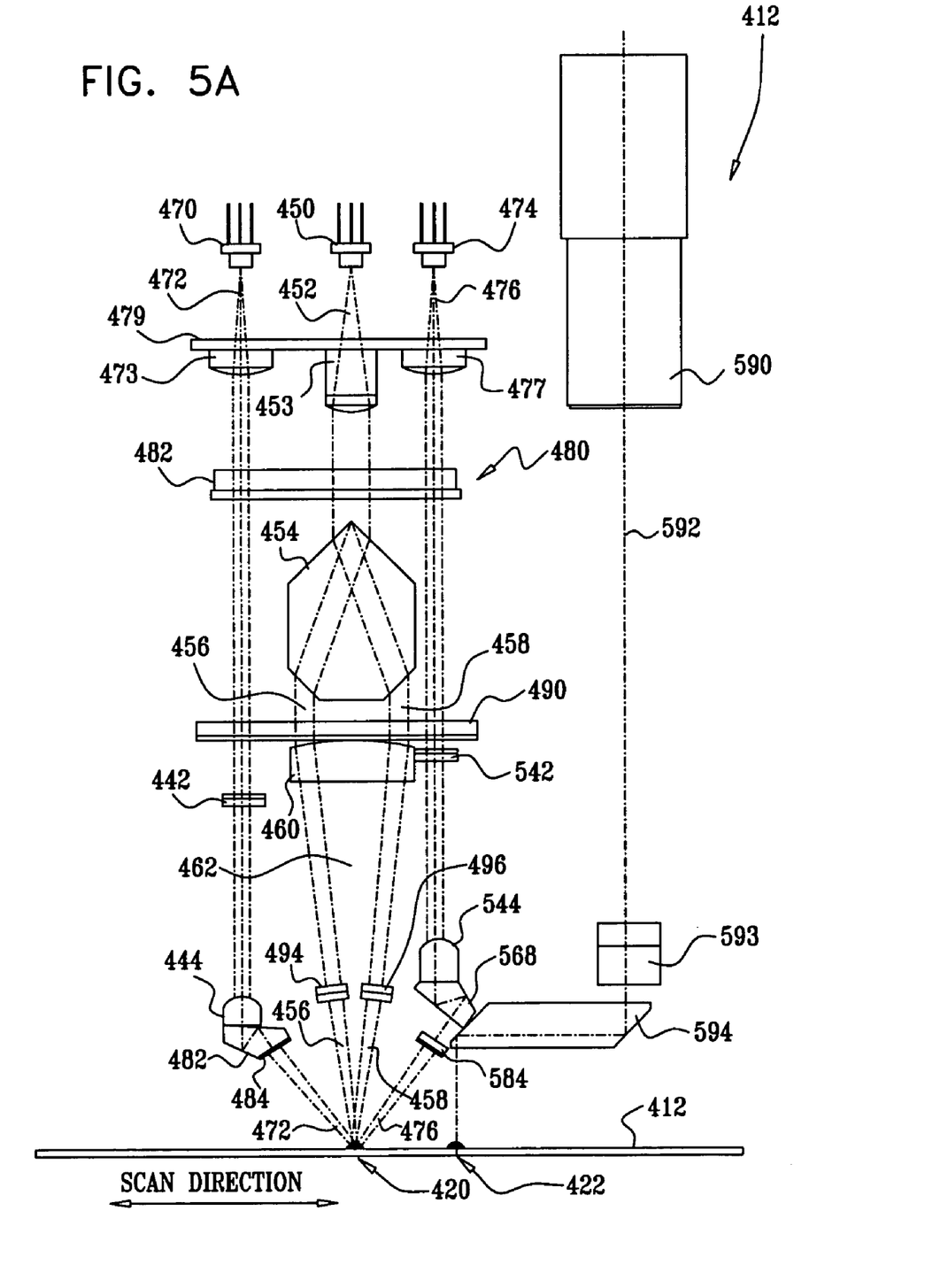
FIG. 5A is a simplified side view illustration and ray trace of the illumination system of FIG. 4.
Figure 5B:
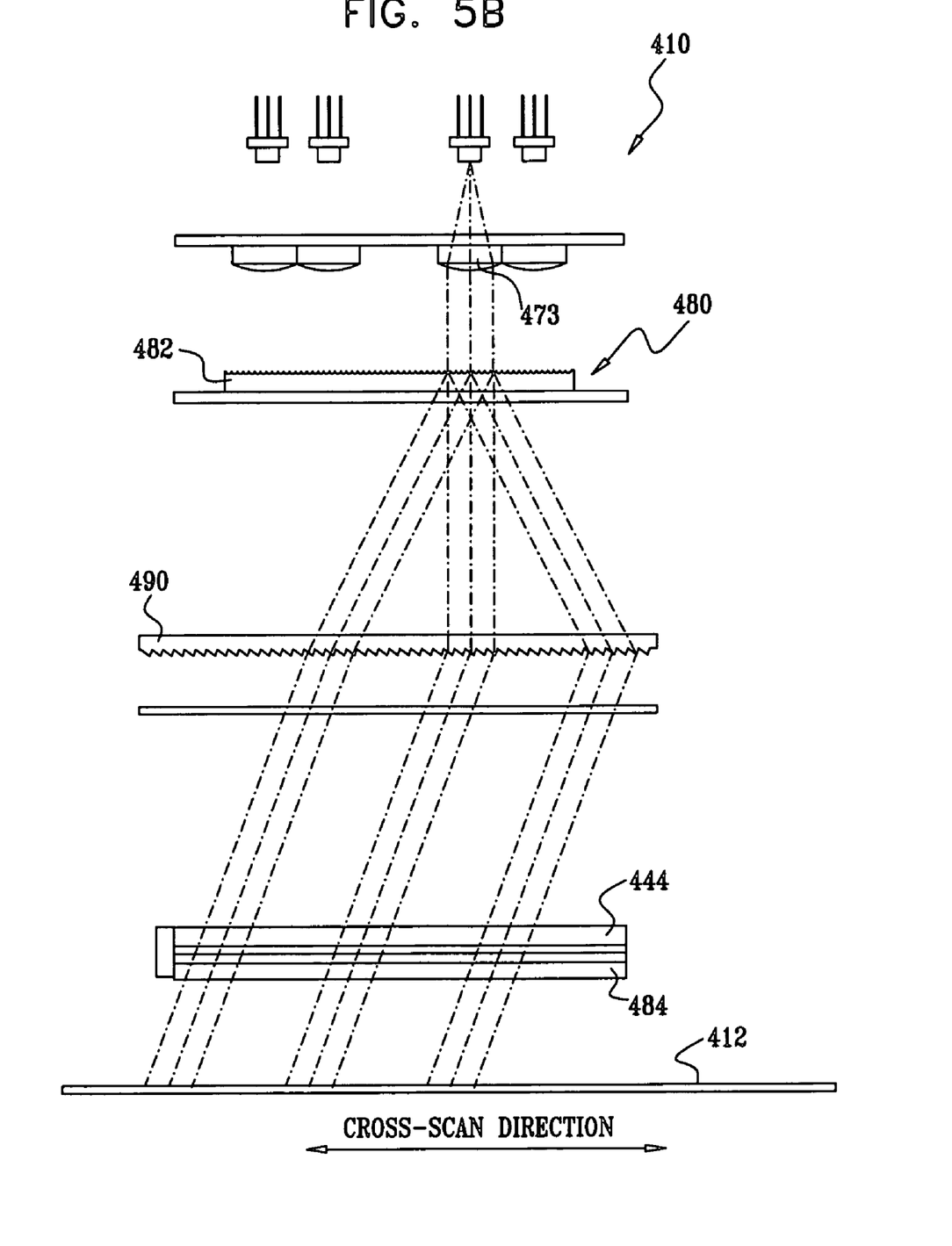
FIG. 5B is a simplified front view illustration and ray trace of the illumination system of FIG. 4.

Reference is now made to FIG. 4 which is a simplified pictorial illustration of an illumination system 400 usable in the system of FIG. 1A, to FIG. 5A is a simplified side view illustration of the illumination system of FIG. 4, and to FIG. 5B is a simplified front view illustration of the illumination system of FIG. 4. System 400 delivers illumination along two light pathways. A first pathway 410 corresponds to pathway 40 in FIGS. 1A and 1B for illuminating a portion of surface 12 with illumination suitable for sensing 2-D information about the surface. A second pathway 412 corresponds to pathway 42 in FIGS. 1A and 1B for illuminating a portion of surface 12 with illumination suitable for sensing topographical information about surface 12.

System 400 delivers high brightness illumination using laser diodes. It is a feature of system 400 that various optical elements are configured and arranged to deliver to an illuminated region generally homogeneous and uniformly angularly distributed concentrated illumination. Each location in the illuminated region generally receives light from a multiplicity of locations in a laser light source virtually functioning as an extended light source. Thus each point location receives laser light appearing to originate from a multiplicity of locations. One result of configuring the optical elements in accordance with an embodiment of the invention, as seen in FIGS. 4-5B, is that despite the use of high brightness lasers output highly coherent light, problematic speckles, typically associated with highly coherent focused illumination, are significantly reduced. Additionally, each location 420 in an illuminated portion 420 (FIGS. 5A and 5B) receives illumination from a multiplicity of illumination angles, as is beneficial for 2-D imaging.

As seen in FIG. 4, a light pathway 410 providing illumination suitable for sensing 2-D information includes two centrally disposed laser diodes 450, each outputting beams 452, four laser diodes 470 disposed along a first side of diodes 450 and outputting beams 472, and an additional four laser diodes 474 disposed along a second side of diodes 450 and outputting beams 476 (FIG. 5A).

Each of beams 452 passes through a collimating lens 453. Each of beams 472 passes through a collimating lens 473, and each of beams 476 passes through a collimating lens 477. Collimating lenses 453, 473 and 477 are, for example spherical lenses, held in place by a light transmissive support 479. Collimating lenses each collimate a beam 452, 472 and 476 associated with the lens.

In accordance with an embodiment of the invention, a diffuser 480, for example a lenticular array defined by a plurality of cylindrical sections 482, is disposed downstream of collimating lenses 453 to receive beams 452, 472 and 476. In the embodiment seen in FIGS. 4-5B, the lenticular array is arranged so that the axis of each cylindrical section 482 is aligned along the scan direction thereby fanning out each beam 452, 472 and 476 in the cross scan direction only but not in the scan direction, as depicted in FIGS. 5A and 5B.

Each of beams 452, output by respective laser diodes 450, impinges on the vertex of a rhombus prism 454. Beams 452 are thus split by rhombus prism into two spatially separated lobes 456 and 458.

Each of lobes 456 and 458 and beams 472 and 476, all of which have been diffused in the cross scan direction, are passed through a lens 490 configured to focus beams in the cross scan direction, but not in the scan direction, as depicted in FIGS. 5A and 5B. Lens 490 may be any suitable cylindrical lens, for example a fresnel lens having a suitable cylindrical cross section, as seen in FIGS. 5A and 5B.

Downstream of fresnel lens 490, lobes 456 and 458 pass through a cylindrical lens 460 extending along an axis in the cross scan direction operative to focus lobes in the scan direction to impinge at location 420 on surface 412. Downstream of cylindrical lens, lobes 456 and 458 each pass through a corresponding diffuser 494 and 496, such as holographic diffusers, expanding lobes 456 and 458 in the scan direction, but not in the cross scan direction, so that lobes impinge at location 420 as rays each having a finite thickness that may be selected in accordance with design parameters and desired width of location 420. As seen in FIG. 5A, each of lobes converges to illuminate portion 420. A wedge shaped gap 462 in the scan direction is thus formed between lobes 454 and 456.

With respect to beam 472, downstream of fresnel lens 490 beam 472 passes through a first diffuser 442, such as a holographic diffuser, further diffusing and homogenizing the beam in the cross scan direction, and a cylindrical lens 444 focusing beam 472 in the scan direction. Beam 472 is deflected by prism 482, and subsequently is diffused in the scan direction by a scan direction diffuser 484, for example a holographic diffuser, attached to an exit face of prism 482 to expand the beam in the scan direction. The expanded beam 472 impinges at location 420 from an angle that is outboard of lobe 456.

With respect to beam 476, downstream of fresnel lens 490 beam 472 passes through a first diffuser 542, such as a holographic diffuser, further diffusing and homogenizing the beam in the cross scan direction, and a cylindrical lens 544 focusing beam 476 in the scan direction. Beam 476 is deflected by prism 586, and subsequently is diffused in the scan direction by a scan direction diffuser 584, for example a holographic diffuser, downstream of prism 586 to expand beam 476 in the scan direction. The expanded beam 476 impinges at location 420 from an angle that is outboard of lobe 458.

It is noted that the respective optical pathways of beams 472 and 476 in the embodiment depicted in FIGS. 4 and 5A are not geometrically symmetrical, although they are, preferably, optically symmetrical. The respective locations of lens 544 and prism 582 have been moved respective of lens 444 and prism 582 in order to accommodate the illumination of portion 420 for sensing topographical information about surface 412.

From the foregoing it is appreciated that in the scan direction, portion 420 is illuminated by light provided from at least 4 general directions from each of lobes 456 and 458, and from beams 472 and 476. Each location 420 additionally receives illumination provided at a plurality of angles in the scan direction, within each of the general directions provided by lobes 456 and 458, and beams 472 and 476. Thus in the scan direction, light is provided at relatively acute angles of illumination by lobes 456 and 458, while additional light is provided at relatively obtuse angles of illumination by beams 472 and 476.

In the cross scan direction, the lenses and diffusers are arranged such that laser light is provided as a virtual extended source providing concentrated light from a multiplicity of directions. It is a feature of an embodiment of the invention that illumination normal to surface 412 is avoided. In the scan direction, illumination normal to the surface is avoided by controlling the geometric angles at which lobes 456 and 458 impinge on the surface. In the cross scan direction the angles of illumination, and avoidance of normal angles of illumination, are controlled though suitable optical design of the diffusers and respective locations of the laser diodes.

Referring to FIGS. 4 and 5A, portion 422 is illuminated along light pathway 412, generally corresponding to light pathway 42 in FIGS. 1A and 1B. At portion 422 a thin elongated beam of illumination is provided along an axis generally perpendicular to surface 412. Light pathway 412 includes at least one high brightness lamp 590, suitably one or more laser diodes, outputting a structured light beam 592 having a generally uniform intensity along its entire length. Beam 592 passes through a cylindrical lens 593 and a periscope 594, operative to translate beam 592 to illuminate the appropriate portion of surface 412 along an axis generally perpendicular to surface 412. Suitable illuminators include Laseris™ structured light generators available from StockerYale, Inc.

Figure 6A:
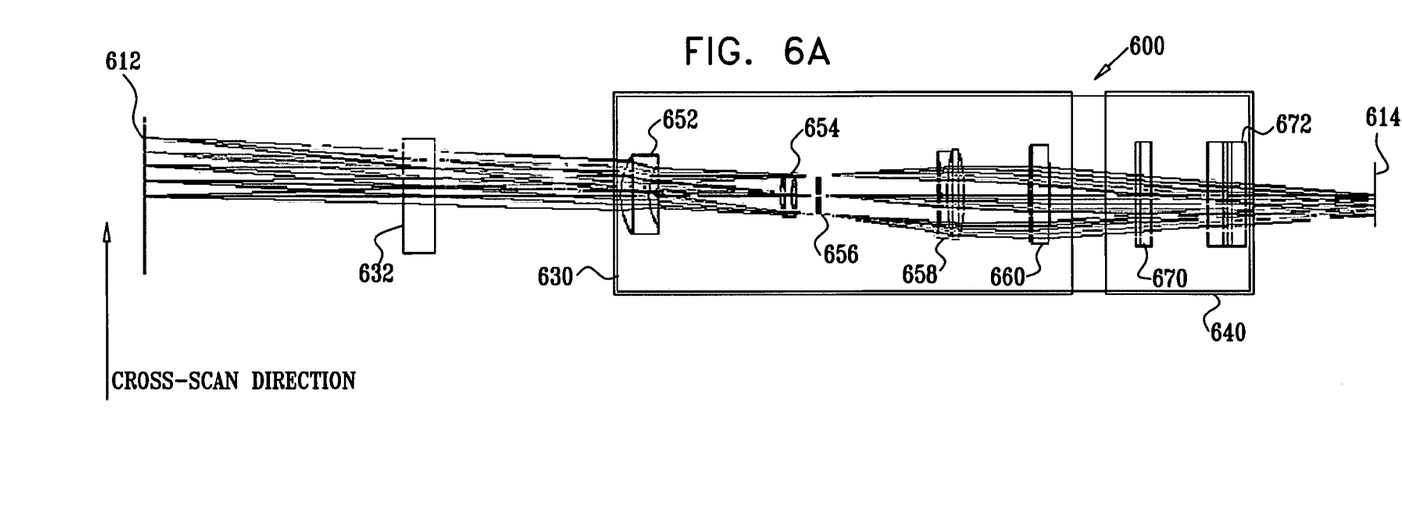
FIGS. 6A and 6B are respective top and side view ray traces of an optical system for simultaneously imaging 2-D and topographical information onto the same sensor in accordance with and embodiment of the present invention.
Figure 6B:
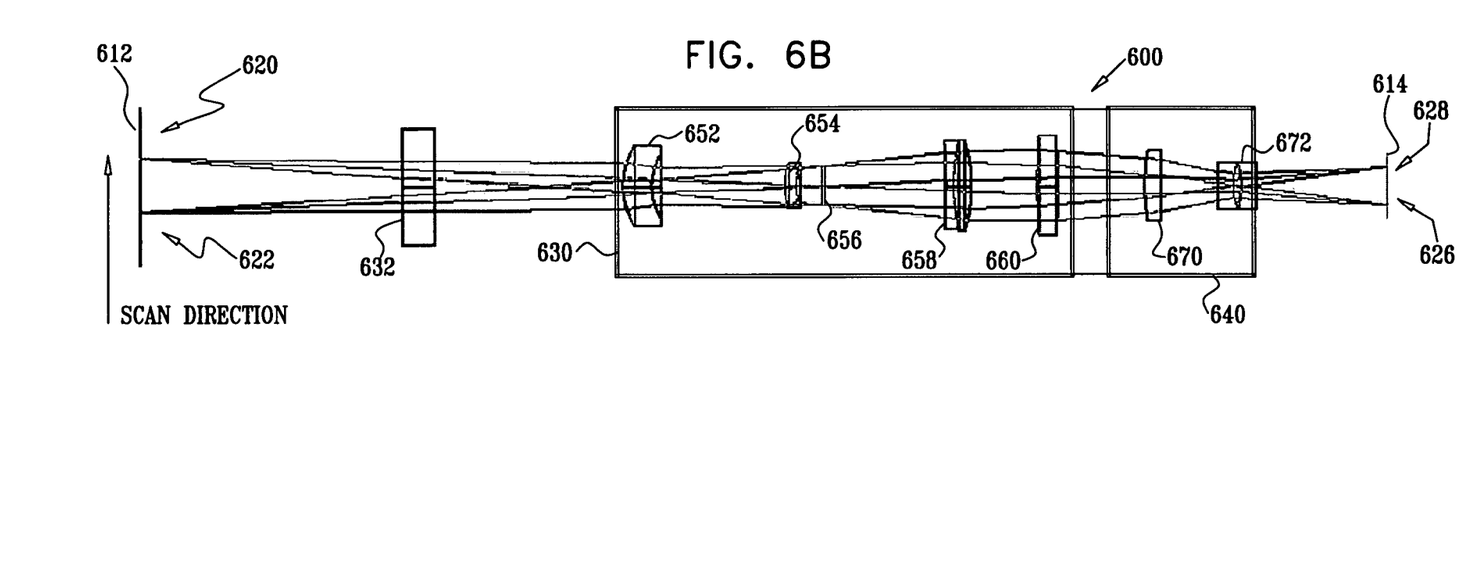

Reference is now made to FIGS. 6A and 6B which are ray traces of an imaging lens 600 for simultaneously sensing 2-D and topographical information on a single sensor array. FIG. 6A is a top view of lens 600 and FIG. 6B is a side view of lens 600.

A surface to be sensed is designated reference numeral 612. 2-D information is sensed at portion 620 of surface 612 and imaged to location 626 on sensor 614. Topographical information is sensed at portion 622 of surface 612 and imaged to location 628. As seen, in FIGS. 6A and 6B, both the sensed 2-D and the sensed topographical information pass through beam combiner 632, corresponding to beam combiner 32 in FIGS. 1A and 1B. Although portions 620 and 622 are set apart from each other and imaged to separate locations on the same sensor array through the same imaging lens 600, the optical elements are configured to maintain an equal optical path length.

Imaging lens 600 includes a first lens array 630 comprising spherical lens elements, and a second lens array 640 comprising cylindrical lens elements. First lens array thus includes a first spherical lens 652, a second spherical lens 654 downstream of first spherical lens, an aperture 656, a third spherical lens 658 downstream of aperture 656 and a fourth spherical lens 660 downstream of third spherical lens 658. Second lens array thus includes a first cylindrical lens 670 and a second cylindrical lens 672 thereby providing different powers of magnification in the respective scan and cross scan directions.

It is appreciated by persons skilled in the art that the present invention is not limited by what has been particularly shown and described hereinabove. Rather the present invention includes modifications and variations thereof which would occur to a person of skill in the art upon reading the foregoing description and which are not in the prior art.

The invention claimed is:

1. Apparatus for sensing information regarding a surface, comprising:
   a first plurality of optical elements arranged to acquire two dimensional information about a surface;
   a second plurality of optical elements arranged to acquire height profile information about said surface;
   said first plurality and said second plurality of optical elements being arranged to simultaneously provide said two dimensional information and said height profile information to at least partially non-overlapping portions of a single sensor array;
   a first plurality of illumination optical elements arranged to illuminate a first portion of said surface with illumination suitable for acquiring two dimensional information about said surface; and
   a second plurality of illumination optical elements arranged to illuminate a second portion of said surface with illumination suitable for acquiring height profile information about said surface;
   wherein said second plurality of illumination optical elements comprises at least one light emitter arranged to illuminate a linear region on said surface from a direction generally perpendicular to said surface.

2. The apparatus claimed in claim 1, wherein said first plurality of optical elements is arranged to acquire said two dimensional information from a first portion of said surface while said second plurality of optical elements acquires said height profile information from a second portion of said surface.

3. The apparatus claimed in claim 2, wherein said first portion of said surface and said second portion of said surface are at least partially non-overlapping.

4. The apparatus claimed in claim 3, wherein said first portion of said surface comprises a first elongated region of said surface, and said second portion of said surface comprises a second elongated region of said surface.

5. The apparatus claimed in claim 2, wherein an optical path distance between said first portion and said single sensor array is equal to an optical path distance between said second portion and said single sensor array.

6. The apparatus claimed in claim 1, further comprising:
a displacer operative to provide mutual displacement between said surface and said first plurality of optical elements during acquisition of said two dimensional information.

7. The apparatus claimed in claim 6, wherein a first portion of said surface whereat two-dimensional information is acquired comprises a first elongated region of said surface, and a second portion of said surface whereat height profile information is acquired comprises a second elongated region of said surface at least partially non-overlapping with said first elongated region.

8. The apparatus claimed in claim 6, said displacer being further operative to provide mutual displacement between said surface and said second plurality of optical elements during acquisition of said height profile information.

9. The apparatus claimed in claim 1, wherein said first plurality of optical elements comprises an imaging lens shared with said second plurality of optical elements, said imaging lens receiving acquired two dimensional information and acquired height profile information.

10. The apparatus claimed in claim 9, wherein said imaging lens is operative to generate an image of a first portion of said surface on said sensor for acquiring two dimensional information corresponding to said first portion, and to generate an image of a line of illumination at a second portion of said surface for acquiring height profile information corresponding to said second portion.

11. The apparatus claimed in claim 1, wherein said first plurality of illumination optical elements comprises at least one light emitter arranged to provide illumination at least some illumination from within a first range of converging angles relative to a first axis, and additional illumination from within a second range of converging angles relative to said first axis.

12. The apparatus claimed in claim 11, wherein said at least one light emitter comprises a plurality of laser diodes.

13. The apparatus claimed in claim 12, wherein said illumination optical elements comprise a diffuser diffusing light from said at least one light emitter along a second axis generally perpendicular to said first axis.

14. The apparatus claimed in claim 13, wherein said diffuser comprises a lenticular array.

15. The apparatus claimed in claim 1, wherein said at least one light emitter comprises at least one laser emitter emitting structured light.

16. The apparatus claimed in claim 1, wherein said first plurality of optical elements is arranged to view a first portion of said surface from a direction generally perpendicular to said surface.

17. The apparatus claimed in claim 16, wherein said second plurality of optical elements is arranged view a second portion of said surface from a direction angled with respect to said surface.

18. The apparatus claimed in claim 17, wherein said first portion is illuminated by illumination provided at a plurality of angles relative to said surface.

19. The apparatus claimed in claim 17, wherein said second portion is illuminated by illumination that is provided from a direction generally normal to said surface.

20. The apparatus claimed in claim 1, wherein said second plurality of optical elements is arranged view a second portion of said surface from a direction angled with respect to said surface.

21. Apparatus for sensing information regarding a surface, comprising:
a first plurality of optical elements arranged to acquire two dimensional information about a surface; and
a second plurality of optical elements arranged to acquire height profile information about said surface during acquisition of said two dimensional information, said second plurality of optical elements comprising an illuminator illuminating a first portion of said surface from a direction being generally perpendicular to said surface.

22. The apparatus claimed in claim 21, wherein said first plurality of optical elements are arranged to acquire said two dimensional information from a direction being generally perpendicular to said surface.

23. The apparatus claimed in claim 22, wherein said second plurality of optical elements are arranged to acquire said height profile information from a direction being generally nonperpendicular to said surface.

24. The apparatus claimed in claim 21, wherein said second plurality of optical elements are arranged to acquire said height profile information from a direction being generally nonperpendicular to said surface.

25. The apparatus claimed in claim 21, further comprising a beam combiner, wherein:
said first plurality of optical elements and said beam combiner define a first optical path for viewing a first portion of said surface from a direction generally perpendicular thereto; and
said second plurality of optical elements and said beam combiner define a second optical path for viewing a second portion of said surface from a generally non-perpendicular angle.

26. The apparatus claimed in claim 25, further comprising:
at least one sensor sensing information about said surface; and
a displacer operative to displace said surface and said sensor relative to each other while said sensor is sensing information.

27. The apparatus claimed in claim 26, wherein said first portion and said second portion are generally non overlapping.

28. The apparatus claimed in claim 26, wherein said at least one sensor comprises a single sensor array operative to sense two-dimensional information corresponding to said first portion at a first location in said sensor array and to sense height profile information corresponding to said second portion at a second location in said sensor array.

29. The apparatus claimed in claim 28, wherein said first location is generally non-overlapping with said second location.

* * * * *